United States Patent [19]

Hlaban

[11] Patent Number: 4,576,597
[45] Date of Patent: Mar. 18, 1986

[54] SANITARY NAPKIN SET

[75] Inventor: James J. Hlaban, Winnebago County, Wis.

[73] Assignee: Kimberly-Clark Corporation, Neenah, Wis.

[21] Appl. No.: 537,922

[22] Filed: Sep. 30, 1983

[51] Int. Cl.⁴ .............................................. A61F 13/16
[52] U.S. Cl. .................................. 604/390; 604/389; 604/385 R
[58] Field of Search .............. 604/385, 389, 390, 366, 604/370

[56] References Cited

U.S. PATENT DOCUMENTS

| | | | |
|---|---|---|---|
| 2,929,379 | 3/1960 | Poulsen | 604/385 R |
| 3,367,334 | 2/1968 | Testa | 604/370 |
| 4,405,310 | 9/1983 | Karami | 604/389 |
| 4,425,130 | 1/1984 | Des Marais | 604/385 R |

Primary Examiner—C. Fred Rosenbaum
Assistant Examiner—Sherri E. Vinyard
Attorney, Agent, or Firm—J. J. Duggan; P. A. Leipold

[57] ABSTRACT

A pair of sanitary napkins is provided each with an absorbent layer and a fluid permeable baffle with adhesive for garment attachment attached thereto. These napkins are put in abutting relationship with a release liner coated on both sides positioned between the adhesive coated bottom surfaces of the respective napkins.

5 Claims, 3 Drawing Figures

1

SANITARY NAPKIN SET

FIELD OF THE INVENTION

This invention relates to a sanitary napkin and particularly to a pair of sanitary napkins sharing a common adhesive release liner.

BACKGROUND OF THE INVENTION

Attempts have been made in the past to provide sanitary napkins which contain wrapped absorbent layers which may be folded upon each other to provide two layers of absorbent protection. U.S. Pat. No. 3,570,492 is representative of such a napkin configuration. The tabbed wrapped napkins disclosed in this patent has means provided in the form of connecting hinge strips which are positioned beyond the ends of the absorbent layers. The napkins are then folded over upon themselves. Another example of such a configuration is disclosed in British Pat. No. 2,107,991 in which two wrapped baffleless napkins are provided with adhesive on the bottom surface of one of the napkins designed to adhere to the top surface of the other napkin. Again, the concept is to use these wrapped baffleless napkins stacked in tandem when one napkin has been used it is discarded and the remaining napkin is left in place by the wearer.

U.S. Pat. No. 3,881,490 discloses a small absorbent pad with a fluid permeable cover and a fluid impervious baffle on the opposing surfaces of the pad. The baffle pad and cover are coterminous at the edges.

These pads are made by means of die-cutting. Die-cutting involves using a die which is shaped like the final exterior configuration and which reciprocally slices a napkin blank formed of the baffle wrap and absorbent batt. The result is very much like a cookie cutter in that a series of identically shaped napkins with the coterminous configuration referred to above are provided.

U.S. Pat. No. 3,881, 490 describes the manufacture of a pantiliner type of product similar to that sold under the KOTEX ® LIGHTDAYS ® trademark by Kimberly-Clark Corporation. These pantiliners are tabless, i.e., they are maintained in place by adhesive attachment means rather than having extended tab ends which are mounted on a supporting belt.

One of the most expensive elements of a tabless sanitary napkin is the adhesive suspension system. The release liner, one of the elements necessary, is generally a paper sheet with a surface providing a defined minimal level for adhesive adhesion. Adhesive is applied to the release liner for subsequent application to the bottom of the napkin. This allows the liner to be maintained in place but readily removable when the product is to be used.

SUMMARY OF THE INVENTION

According to this invention a pair of sanitary napkins with adhesive attachment means is provided. The adhesive attachment means utilize a single common release liner.

According to the method of this invention a sanitary napkin blank is provided by attaching a thermoplastic fluid impervious baffle to one side of the batt of absorbent material. A release liner having two release treated surfaces with adhesive applied to each of these surfaces is then married to the baffle side of the napkin blank. A second napkin blank is provided with the exposed baffle side positioned in contact with the second adhesively coated surface of the release liner in registry. Pressure and/or heat is subsequently applied to provide the minimum adhesive tack necessary to bind the release liner to the sanitary napkin blanks and the blanks are die-cut to form a pair of sanitary napkins having coterminous baffles, absorbent layers and wraps.

DETAILED DESCRIPTION OF THE INVENTION AND DRAWINGS

Figure 1:
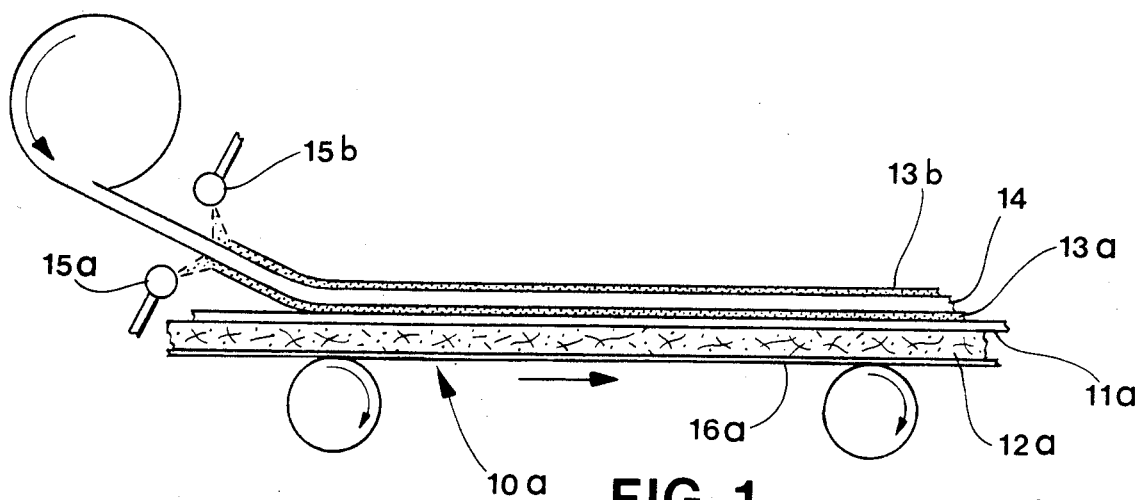
Figure 2:
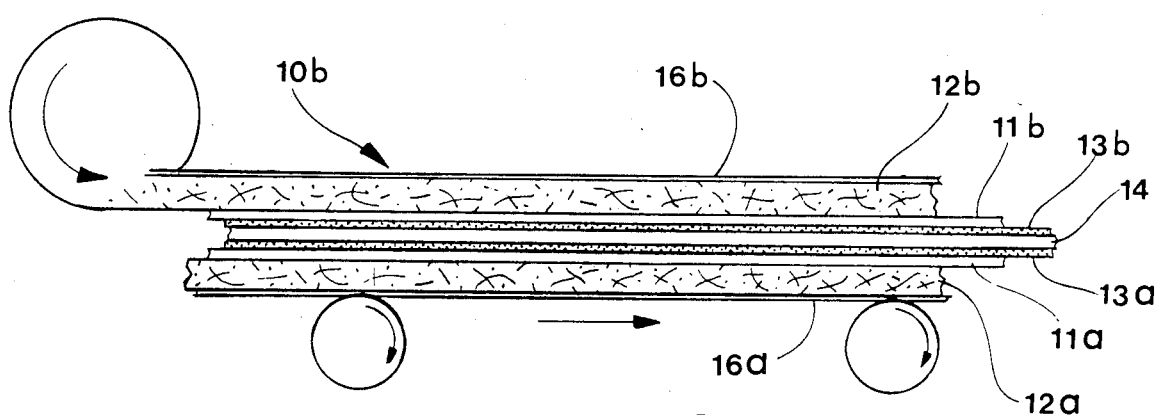
Figure 3:
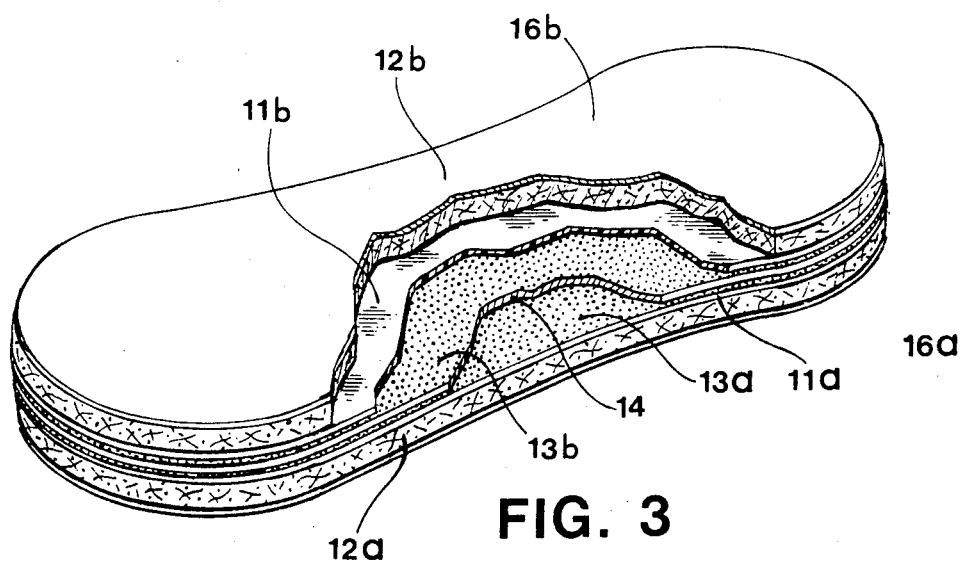

The invention can more readily be understood by reference to the drawings in which FIGS. 1 and 2 are cross-sectional views of the napkin blanks formed according to the process of this invention and FIG. 3 is a plan view partially in cross-section of the pair of sanitary napkins made in accordance with this invention.

Initially a sanitary napkin blank is made by attaching a fluid impermeable baffle to an absorbent layer. This can be seen from FIG. 1. Such a napkin blank having cover 16a, absorbent layer 12a, and baffle 11a is married with a release liner 14 which has been previously treated with a suitable release coating on both sides, e.g., silicone. The release liner 14 has been coated with an adhesive pattern represented generally at 13a and 13b on the upper and lower faces thereof by extruder nozzles 15a and 15b positioned to apply adhesive to the upper and lower surfaces prior to the release liner 14 contact with napkin blank 10a.

After this contact has occurred, a second napkin blank 10b having cover 16b, an absorbent layer 12b and baffle 11b is applied in registry with napkin blank 10a and release liner 14 so that baffle 11b is adjacent adhesive layer 13b on release liner 14 in the same manner that baffle 11a is adjacent the adhesive layer 13a.

After napkin blanks 10a and 10b have been positioned in registry surrounding release liner 14 heat and/or pressure is applied to either of the napkin blanks 10a or 10b to provide for sufficient releasable attachment for each of the napkins. The attached combination, according to the method of this invention, is die-cut to produce the shaped pair of napkins depicted at FIG. 3. These napkins pairs are then packaged and sold. When the consumer wishes to use the first of a pair of napkins she merely removes the napkin from the release liner leaving the release liner in place to protect the adhesive surface of the second napkin. When the second napkin of the pair is utilized the release liner may then be discarded.

The napkin pair and the method of this invention allows for the utilization of substantial cost savings by not only eliminating a release liner, but cutting twice as many napkins with the same cutting action.

The method of this invention is particularly preferred with the smaller, i.e., liner type napkins but can be used with any full-sized die-cut napkin with the same cost benefits.

Of course it is within the teachings of this invention to utilize napkin pairs which have fluid permeable covers. The cover, as opposed to a wrap, merely extends over the top or body facing surface of the napkin and does not encircle the other napkin components. In fact, such a wrap may generally be desirable for purposes of napkin integrity and comfort although certain absorbent materials such as those which are composites of thermoplastic fibers and other absorbent fibers may not require a wrap for purposes of integrity or softness.

What is claimed is:

1. A method for making sets of die-cut sanitary napkins comprising:
   providing first and second webs each comprised of a layer of fluid absorbent material having two faces and a layer of fluid impermeable baffle material affixed to one face of said layer of absorbent material, and a third web of a release liner material having two faces,
   coating both faces of said release liner web with an adhesive pattern,
   combining said first and second webs with said release liner web by placing said baffle material on said first web against the adhesive pattern on one face of said release liner web, and placing said baffle material of said second web against said adhesive pattern on the other face of said release liner web, said three webs being in general registry, and
   die cutting said combined first, second and third webs into sanitary napkin sets having two sanitary napkins sharing a common release liner.

2. A sanitary napkin set made according to the method of claim 1.

3. The sanitary napkin set of claim 2 wherein each of said first and second webs further includes a layer of fluid permeable cover material over the other face of said layer of absorbent material.

4. A method for making sets of sanitary napkins comprising:
   providing first and second webs each comprised of a layer of fluid absorbent material having two faces and a layer of fluid impermeable baffle material affixed to one face of said layer of absorbent material, and a third web of a release liner material having two faces,
   coating both faces of said release liner web with an adhesive pattern,
   combining said first web with said release liner by placing the adhesive pattern on one face of said release liner web against said baffle material of said first web,
   combining said second web with said release liner web by placing said baffle material of said second web against the adhesive pattern on the other face of said release liner web,
   applying pressure to removably attach said combined first and second webs to said release paper, and
   die-cutting said attached first, second and third webs to form sets of sanitary napkin pairs sharing a common release liner.

5. A sanitary napkin set made according to the method of claim 4.

* * * * *